United States Patent
Anczurowski et al.

[11] 3,945,386
[45] Mar. 23, 1976

[54] DISPOSABLE DIAPER

[75] Inventors: Edward Anczurowski, Dollard des Ormeaux; Brian E. Julien, Pierrefonds, both of Canada

[73] Assignee: Domtar Limited, Canada

[22] Filed: Aug. 8, 1972

[21] Appl. No.: 278,729

[52] U.S. Cl. ............................................... 128/287
[51] Int. Cl.² ........................................ A61F 13/16
[58] Field of Search ........... 128/284, 286, 287, 290, 128/296, 295

[56] References Cited
UNITED STATES PATENTS

| | | |
|---|---|---|
| 2,024,976 | 12/1935 | Mathey et al. .................. 128/290 R |
| 2,923,298 | 2/1960 | Dockstader et al. ................. 128/296 |
| 3,046,986 | 7/1962 | Harwood .......................... 128/290 R |
| 3,180,335 | 4/1965 | Duncan et al. ...................... 128/287 |
| 3,221,738 | 12/1965 | Ekberg et al. ...................... 128/287 |
| 3,344,789 | 10/1967 | Arnold et al. ....................... 128/295 |
| 3,636,952 | 1/1972 | Gedrge .............................. 128/287 |
| 3,665,921 | 5/1972 | Stumpf .............................. 128/287 |

*Primary Examiner*—Ronald L. Frinks
*Attorney, Agent, or Firm*—C. A. Rowley

[57] ABSTRACT

A disposable diaper constructed to keep the hydrophobic diaper facing sheet relatively dry by interposing a perforated plastic film between the facing and the absorbent pad.

1 Claim, 6 Drawing Figures

DISPOSABLE DIAPER

FIELD OF THE INVENTION

The present invention relates to disposable diapers, more specifically the present invention relates to a structure for a disposable diaper wherein a perforated plastic sheet is interposed between the absorbent pad and the facing layer contacting the infant to tend to reduce the moisture content of the layer.

DESCRIPTION OF THE PRIOR ART

Conventional disposable diapers normally consist of a facing layer which contacts the infant (usually made of a suitable hydrophobic non-woven material) overlying a pad of absorbent material such as wood pulp which in turn overlies an impervious plastic film. The facing sheet directly contacts the pad and thus nothing impedes the migration of moisture back into the facing whereby the baby does not stay dry and as a result the baby may suffer from diaper rash or the like. Generally, the more hydrophobic the facing sheet, the less moisture it will retain, the quicker it will tend to dry and the less tendency it will have a rewet thereby reducing the probability of the baby suffering from a diaper rash, however, even with a relatively hydrophobic facing sheet, the moisture content may be quite high.

It has been proposed to use as the inner facing sheet of the diaper a plastic film provided with depressions and minute perforations. The film is forced into the absorbent pad of the diaper by application of heat and pressure to form the depressions and minute perforations (see Canadian Pat. No. 731,336 issued Apr. 5, 1966 to Ekberg). Minute perforations may tend to ipair moisture penetration and may cause moisture to accumulate in the depressions. Also, the use of a plastic layer in direct contact with the baby's skin is not generally satisfactory.

It is thus the object of the present invention to reduce the moisture contact of the diaper facing sheet which contacts the baby.

SUMMARY OF THE INVENTION

Broadly, the present invention comprises a diaper having an absorbent pad, a hydrophobic body-contacting layer and a perforated plastic film interposed between the absorbent pad and the hydrophobic layer.

BRIEF DESCRIPTION OF THE DRAWINGS

Further features, objects and advantages will be evident from the following detailed description taken in conjunction with the accompanying drawings in which.

DESCRIPTION OF THE PREFERRED EMBODIMENTS

Figure 1:
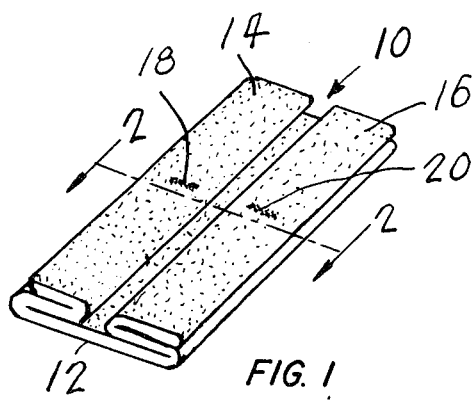
FIG. 1 is an isometric view of one form of diaper incorporating the present invention.

Referring to FIg. 1, the general structure of a diaper 10 comprises essentially a pad portion 12 with a pair of box pleated sections 14 and 16 one on each side thereof. The box pleats may be secured together in the central region as designated by 18 and 20 so that the diaper will maintain its narrow width in this region which conforms with the crotch of the infant while the remainder of the box pleat may be expanded to extend about the infant's waist to facilitate securing the diaper in position.

Figure 3:
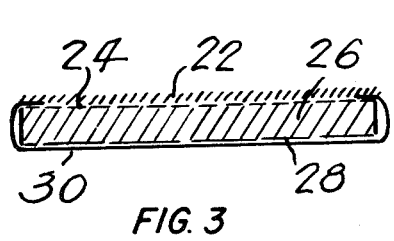
FIG. 3 is a slightly enlarged view of the cross-section of diaper before folding.
Figure 2:
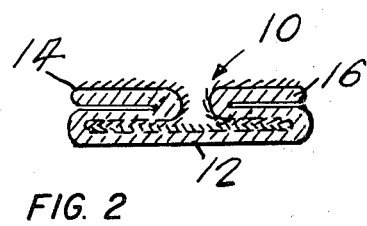
FIG. 2 is a section along the line 2—2 of FIG. 1.

The illustrated diaper includes a hydrophobic body-contacting diaper facing sheet 22, which preferably is a hydrophobic non-woven material, overlying a perforated plastic film 24 which in turn overlies an absorbent pad 26. The absorbent pad 26 may be formed of cellulosic fibrous wadding or a plurality of layers of tissues or any other suitable absorbent pad. Also, in the illustrated arrangement, there is provided a layer 28 of tissue or the like interposed between the pad 26 and the impervious backing member 30 and the backing member 30 is shown wrapped about the ends of the pad 26 to enclose the pad on two sides (see FIG. 3). The film 24 and backing member 30, for example, may be made of polyethylene. The various layers are shown enlarged in FIG. 4.

Figure 4:
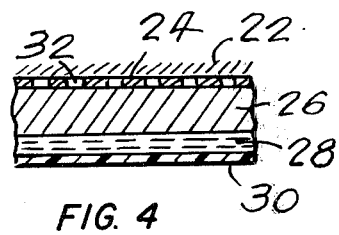
FIG. 4 is a large section of a portion of the diaper shown in FIG. 3.

The perforations 32 in the perforated film 24 are preferably approximately one-eighth inch in diameter and are spaced apart about three-eighths inch. The spacing is not critical but it is important that the area between the perforations be sufficiently small to prevent the formation of puddles. Similarly this size of the perforations is not critical, however, they should be sufficiently large to permit easy penetration of the urine while limiting contact between the facing 22 and the pad 26 to inhibit migration of the liquid from the pad 26 back to the diaper facing, i.e., the diaper facing preferably should bridge the perforations without sagging into contact with the pad 26 thereby limiting the contact between the diaper facing 32 and the pad 26 (substantially as shown in FIG. 4) and thus the opportunity for liquid to migrate from the pad 26 back into the facing 22.

The perforations may be arranged in any suitable pattern, for example as described above in a uniform arrangement on ⅜ inch centres. It has been found that the perforations are only essential in the central area of the diaper. Urine tends to migrate through the pad between the imperforate areas of the film 24 (i.e., to the areas in sections 14 & 16 at the longitudinal ends of the diaper) but none escapes to the diaper facing in the imperforate areas.

Generally, the perforations should be between about 1/16 and ⅜ inch diameter and should be on about ¼ to ¾ inch centres. Where slits or slots are used instead of perforations, the width of the opened slit should be between about one-sixteenth and three-sixteenth inches.

Figure 5:
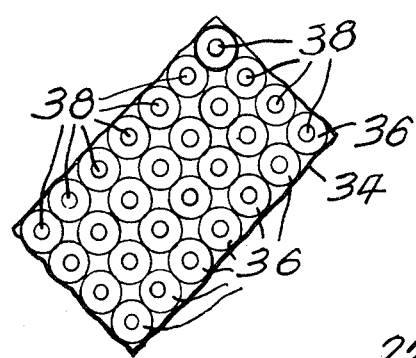
FIG. 5 is a plan view of a perforated plastic film suitable for use in the present invention.

The film 34 shown in FIG. 5 is adapted to replace the film 24 in the FIG. 1 to 4 inclusive embodiment. This film 34 is provided with a plurality of indentations 36 each of which is perforated at its lower-most point as indicated at 38 (see also FIG. 6) to form funnel-like sections tapering toward the pad.

Figure 6:
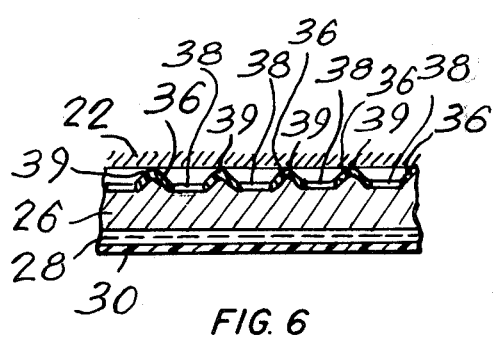
FIG. 6 is a section through the diaper incorporating the embossed film of FIG. 5.

FIG. 6 shows enlarged cross-section of a portion of a diaper incorporating the plastic film 34 illustrated in FIG. 5. As shown, the nonwoven 22 overlies the film 34 and is supported on the peaks 39 between the depressions 36. The apertures 38 at the bottom of the depressions 36 communicate directly with the pad 26 so that urine enters the depressions 36 and due to their funnel-like shape is quickly moved down into the apertures 38 into contact with the pad 26 where it is absorbed. With this arrangement fewer perforations are required since the funneling effect of the indentations 36 better ensures that the urine reaches the perforations 38 and thus the pad 26. The size and number of perforations 38, of course, should be sufficient to ensure that the urine passes quickly into the pad 26.

It will be noted in FIG. 6 that the depressions 36 improve the separation between the facing 22 and the pad 26 and thus make migration of liquid from the pad 26 back to the non-woven 22 even more difficult thereby tending to improve the dryness of the facing.

The structure of FIG. 6 preferably is manufactured by indenting and perforating the film 34 in situ overlying the pad 26 before the non-woven 22 is applied. One convenient method of forming the indentations is to use a heated embossing tool to press the film 34 into the pad 26 to form the depressions 36 and simultaneously perforate the film as indicated at 38.

EXAMPLE

Four inch samples containing about 4 ½ grams of pulp were cut from diapers and wetted by releasing measured amounts of water to incorporate in the pulp up to about 8 grams of water per gram of pulp. This is clearly more than the normal amount of moisture found in a wet diaper (normally about 2–4 grams water/grams of pulp). In the tests of diapers incorporating the present invention, a 1 mil thick polyethylene sheet with ⅛ inch holes on ⅜ inch spacing was used. Two different diaper non-woven facing sheets were examined (one more hydrophobic than the other) and the moisture content of the non-woven was measured at 0, 15, 30 and 45 minute intervals. The results of these tests are given in Table I.

woven and the absorbent pad after 15 minutes reduced the total moisture content of the facing sheet significantly. It will also be apparent that the characteristics of the facing sheet are extremely important in determining its moisture content. Non-woven facing A (the more hydrophobic of the two tested) after 15 minutes had a moisture content of .20 gms/gm pulp, whereas non-woven facing B still retained 1.56 gms/gm with the moisture content of facing B always being considerably higher than A. In any event the results clearly indicate that the present invention improves the performance of both the non-woven facing sheets A & B.

It is believed that the diaper facing is maintained drier in diapers incorporating the present invention by inhibiting migration of water from the absorbent pad back into the facing.

Modifications may be made without departing from the spirit of the invention as defined in the appended claims.

We claim:

1. A diaper comprising a hydrophobic diaper facing sheet, an absorbent pad, a discrete perforated plastic film interposed between said facing sheet and said pad, an impervious backing sheet covering the side of said pad remote from said facing sheet, said pad and said discrete perforated plastic film being in intimate contact to ensure body fluids passing through said perforations immediately contact said pad, said perforated film being indented about each perforation thereby to provide a funnel like surface surrounding each perforation, said funnel like surface tapering in toward said pad, said perforations being sufficiently large to permit easy penetration of body fluids yet sufficiently small that the facing sheet bridges each of said perforations, each said perforation is equivalent in open area to a hole one-sixteenth to three-eighths inch in diameter and said perforations are located on centers spaced between one-fourth and three-fourths of an inch, said film substantially eliminating contact between said hydrophobic facing sheet and said pad whereby migration of said fluids from said pad back into said hydrophobic facing sheet is impaired.

TABLE I

| Diaper Facing Sheet | gms H₂O gm pulp | Perf. Film | Time Minutes | | | |
|---|---|---|---|---|---|---|
| | | | 0 | 15 | 30 | 45 |
| | | | Residual water gms/gm in diaper facing | | | |
| A (more hydrophobic) | 2.2 | No | 0.34 | 0.29 | 0.10 | 0.10 |
| | | Yes | 0.40 | 0.07 | 0.04 | 0.04 |
| A  " | 4.1 | No | 0.88 | 0.64 | 0.30 | 0.15 |
| | | Yes | 0.99 | 0.15 | 0.03 | 0.03 |
| A  " | 6.1 | No | | 1.45 | 1.35 | 1.10 |
| | | Yes | | 1.43 | 0.60 | 0.43 |
| A  " | 8.1 | No | | 3.70 | 3.40 | 3.10 |
| | | Yes | | 2.40 | 2.10 | 1.70 |
| B (less hydrophobic) | 2.2 | No | | 1.56 | 1.08 | 0.87 |
| | | Yes | | 1.45 | 0.83 | 0.42 |

It is evident that in substantially all cases examined, the perforated plastic film interposed between the non-

* * * * *